US012758424B2

(12) United States Patent
Hacker

(10) Patent No.: US 12,758,424 B2
(45) Date of Patent: Oct. 13, 2026

(54) PLANNING METHODS AND DEVICES FOR PRECISELY CHANGING A REFRACTIVE INDEX

(71) Applicant: Carl Zeiss Meditec AG, Jena (DE)

(72) Inventor: Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1212 days.

(21) Appl. No.: 17/633,195

(22) PCT Filed: Aug. 5, 2020

(86) PCT No.: PCT/EP2020/072069

§ 371 (c)(1),
(2) Date: Oct. 11, 2022

(87) PCT Pub. No.: WO2021/023799

PCT Pub. Date: Feb. 11, 2021

(65) Prior Publication Data

US 2025/0352393 A1 Nov. 20, 2025

(30) Foreign Application Priority Data

Aug. 7, 2019 (DE) ..................... 10 2019 211 861.5

(51) Int. Cl.
*A61F 9/008* (2006.01)
*A61B 34/10* (2016.01)

(52) U.S. Cl.
CPC .......... *A61F 9/00804* (2013.01); *A61B 34/10* (2016.02); *A61F 9/00814* (2013.01)

(58) Field of Classification Search
CPC ... A61F 9/00804; A61F 9/00814; A61B 34/10
See application file for complete search history.

(56) References Cited

U.S. PATENT DOCUMENTS

2008/0208525 A1* 8/2008 Kikawa .............. G01N 21/4795 702/172
2010/0228345 A1 9/2010 Bille
(Continued)

FOREIGN PATENT DOCUMENTS

DE 102005013558 A1 9/2006
DE 102005032041 A1 1/2007
(Continued)

OTHER PUBLICATIONS

International Search Report for PCT/EP2020/072069, mailed Oct. 9, 2020, 5 pages.
(Continued)

*Primary Examiner* — Carl H Layno
*Assistant Examiner* — Aya Ziad Bakkar
(74) *Attorney, Agent, or Firm* — DeWitt LLP

(57) ABSTRACT

Planning methods and a planning device for generating control data for a control unit of a laser treatment device for changing a refractive index in the treatment zone of a transparent organic material, a laser treatment device, and a computer program product. The invention facilitates precise correction of the refractive index and thus adjusts the previously planned profile of the refractive index in the transparent organic material region to be treated during the treatment. Even highly locally limited refractive index variations are correctable. Data describing the actual behavior of the indicator structure in the examination zone are considered, and control data is output to the control unit at specified intervals during the treatment of the material in the treatment zone, wherein the last described behavior of the indicator structure in the examination zone is constantly used as new actual behavior of the indicator structure to ascertain the control data.

23 Claims, 4 Drawing Sheets

(56) References Cited

U.S. PATENT DOCUMENTS

| | | | | |
|---|---|---|---|---|
| 2019/0183678 | A1* | 6/2019 | Rathjen | A61F 9/00814 |
| 2019/0193208 | A1* | 6/2019 | Kalli | B23K 26/0006 |

FOREIGN PATENT DOCUMENTS

| | | | | |
|---|---|---|---|---|
| DE | 102016208011 | A1 | 11/2007 | |
| DE | 602 21 902 | T2 | 5/2008 | |
| EP | 2032102 | A2 | 3/2009 | |
| WO | WO 2006/117195 | A1 | 11/2006 | |
| WO | WO 2008/002795 | A2 | 1/2008 | |
| WO | WO 2018/052455 | A1 | 3/2018 | |
| WO | WO-2019147952 | A1 * | 8/2019 | B29D 11/023 |

OTHER PUBLICATIONS

English translation of International Search Report for PCT/EP2020/072069, mailed Oct. 9, 2020, 3 pages.

Len Zheleznyak, ophthalmology/femtosecond lasers: LIRIC: Next-Generation refractive laser surgery, http://www.biopticsworld.com/articles/print/volume-9/issue-11/ophthalmology-femtosecond-lasers-liric-next-generation-refractive-laser-surgery.html.

R.W. Gerchberg and W.O. Saxton, "A Practical Algorithm for the Determination of Phase from Image and Diffraction Plane Pictures", Optik 35, 237 (1971).

* cited by examiner (Stand der Technik)

PLANNING METHODS AND DEVICES FOR PRECISELY CHANGING A REFRACTIVE INDEX

RELATED APPLICATIONS

This application is a National Phase entry of PCT Application No. PCT/EP2020/072069 filed Aug. 5, 2020, which application claims the benefit of priority to DE Application No. 10 2019 211 861.5 filed, Aug. 7, 2020, the entire disclosures of which are incorporated herein by reference.

TECHNICAL FIELD

The present invention relates to planning methods and a planning device for generating control data for a control unit of a laser processing apparatus for changing a refractive index in the processing zone of a transparent organic material. The present invention furthermore relates to a laser processing apparatus and a computer program product.

BACKGROUND

Conventional refractive corrections such as laser vision corrections (LVC) or intraocular lens (IOL) implantations suffer from residual errors in the actually attained correction. These deviations can be the result of measurement errors prior to the operation, of tolerances in the correction itself or of variations, slight eye movements, etc. during the operation, but can often also be due to patient-specific properties, for example due to scarring which is patient specific and hence difficult to predict, healing, different tissue properties or an ambient or patient-specific hydration state of the cornea. On account of the inaccurate refraction correction frequently resulting therefrom, it is currently often necessary to implement a subsequent refraction correction (such as spectacles or contact lenses), or even a correction by surgery.

By way of example, a laser vision correction can be adapted by subsequent laser vision treatment, for example excimer LASIK. However, correcting the IOL results is more difficult. In this case, too, laser vision correction of the cornea is often the only remaining choice or alternative to spectacles.

Therefore, an interesting alternative lies in the adjustment of optical elements such as IOLs, and optionally also of contact lenses or spectacles, by way of a postsurgical refractive index adjustment. By way of example, this is possible by the use of UV-sensitive polymers for the production of these optical elements, for example as proposed in DE 602 21 902 T2.

A relatively novel approach for such corrections lies in the laser-induced change in the refractive index (laser-induced refractive index change, LIRIC) and/or the change of the refractive index in the tissue (intra-tissue refractive index change, IRIS), in such a way that there is a noninvasive refractive correction of the refractive index (of a material) in the tissue post-surgery by use and appropriate modification of an adjustable refraction component in the material or tissue.

FIGS. 1*a* and 1*b* show such a state-of-the-art laser-induced change in the refractive index (LIRIC) in a region of the cornea 4 or in an intraocular lens 5 of a patient's eye 3 (Len Zheleznyak, ophthalmology/femtosecond lasers: LIRIC: Next-Generation refractive laser surgery, http://www.bioopticsworld.com/articles/print/volume-9/issue-11/ophthalmology-femtosecond-lasers-liric-next-generation-refractive-laser-surgery.html). The application of an excimer laser or femtosecond laser is otherwise usually used to ablate the surface of the cornea 4, or else incisions in the cornea 4 are performed by application of photodisruption. However if, for example, a focused femtosecond laser beam 2, 2' is used at a substantially lower pulse energy (that is to say, for example, at a pulse energy 100 to 1000 times lower depending on the point of action, that is at 1/100 to 1/1000 of the pulse energy), the introduction of the pulsed radiation 2, 2' results in this pulse energy changing the refractive index of the tissue, or else of an artificial optical element, at this point 17 in a targeted manner in the cornea 4 or else in deeper structures such as a lens, in particular also a natural or artificial intraocular lens 5, without producing an incision.

A problem that is yet to be solved is that of setting a really precise refractive index profile in a single treatment method, that is to say design a change in the refractive index in the treated region of the tissue/the artificial structure such that the result corresponds to the previously planned profile of the refractive index, by application of which the refractive error is substantially completely corrected.

Known solutions use nomograms in order to approximately generate the desired change profile of the refractive index by applying a laser scanning pattern calculated in advance, which comprises both spatial information and information regarding performance parameters at the respective position of the focal point of the focused pulsed laser beam. Then, the results are checked post surgery by measuring the residual refractive errors (e.g., by wavefront measurement methods) and are subsequently corrected by later correction of the determined residual refractive error in a further treatment (at a very different point in time and usually also using different methods). Thus, this then requires a further implementation of a treatment method. Moreover, the measurements of the residual refractive error can consider only the whole or at least the predominant part of the treated tissue zone simultaneously and do not allow determination and correction of local variations (e.g., at a single treated point). Therefore, the current state-of-the-art does not allow a correction of the local refractive index variations of unknown strength, for example. In addition to absorption and scattering, such local refractive index variations can also be a cause of so-called "floaters" or "mouche volantes" in the vitreous humor of the eye. Below, the term "floater" is intended to be used as a synonym for local refractive index variations, independent of the location.

Here, different factors before and during the treatment, which are "not completely controllable or only controllable with great difficulties", prevent the substantially complete correction of the refractive error using the tools available to date. These factors include certain tissue properties (for example the hydration which varies the refractive index of the tissue, systemic or locally applied medicaments, irradiation, previous illnesses, that is to say natural or previously artificially generated refractive index gradients or local refractive index variations), laser properties (power fluctuations, focus deformation as a result of entry into tissue layers) or ambient parameters (absorption, tissue movement/tissue vibrations, pressure or stress on the tissue).

SUMMARY OF THE INVENTION

Example embodiments of the present invention address many of the above discussed problems and describe an apparatus and methods for facilitating a precise correction of the refractive index, that is to say actually set the (ideal) profile of the refractive index, planned in advance, in the region to be processed of a transparent organic or inorganic material, in particular of a patient's eye, despite disturbances by factors during the treatment that are difficult to control. In particular, very locally restricted refractive index variations whose extent can only be predetermined with difficulties should also be corrected, as is the case, for example, for virtually transparent floaters in the vitreous humor of a patient's eye.

An example planning method for generating control data for a control unit of a laser processing apparatus for changing a refractive index in a processing zone of a transparent organic or inorganic material, for example a patient's eye, comprises the following steps:

The actual behavior of an indicator structure in an examination zone arranged in an optical path downstream of a processing zone of the transparent organic or inorganic material transilluminated by examination radiation is characterized. Such a "behavior" can be for example an optical appearance, such as a luminous intensity distribution or a light phase distribution, a shadow cast, an interference pattern or an OCT signal distribution, or the combinations thereof. In this case, the indicator structure can be arranged directly in the examination zone or else can represent a mapping of a structure in the processing zone into the examination zone (i.e., represent a virtual indicator structure).

The target behavior of the indicator structure in the examination zone is defined. Such a "definition" can be the confirmation of an already stored target behavior, but also a definition of the target behavior is possible at this point on account of a formulation of the physician (for example, a desired change in overall refraction or a local optical path length change, that is to say the course of a refractive index profile over a large region or the refractive index profile over a beam path at a specific point, of an appearance image obtained after attaining a homogeneous refractive index in the processing zone, in particular by adjusting a restricted region of the processing zone to its direct surroundings in the processing zone, etc.). The planning method then considers these wishes in order to "convert" them into a target behavior. In the simplest case, this can be the "automatic" definition of the "target behavior" by a machine if the object of the planning method is that of achieving a homogeneous distribution of the refractive index in the processing zone. Ultimately, this specifies—either manually or automatically—an attainable and testable target behavior in the examination zone.

Subsequently a change profile of the refractive index in the processing zone is determined from the difference between the actual behavior and the target behavior of the indicator structure in the examination zone. This can be easily implemented as follows: The actual behavior of the indicator structure in the examination zone is determined from the actual distribution of the refractive index in the processing zone—from a deviation of the actual behavior of the indicator structure in the examination zone, it is therefore possible to deduce at least a deviation from the target distribution of the actual distribution of the refractive index in the processing zone. However, a unique deduction of a certain refractive index profile from the actual behavior is not always uniquely possible since different refractive index profiles may generate the same or very similar actual behavior, and even optical path length changes may be realized by different combinations of refractive index changes and processing zone lengths. However, a certain one-, two- or three-dimensional target profile of the refractive index in the processing zone always corresponds to an expected target behavior of the indicator structure in the examination zone, and so there always is a solution, but optionally a plurality of viable solutions (within given error tolerances), which can be tracked. From the difference between the target behavior and actual behavior, for example of the two intensity distributions, it is sometimes possible to directly deduce a change profile of the refractive index, said change profile specifying the absolute value by which the refractive index could be changed at what position (x, y, z) in the processing zone in order to obtain the target behavior. However, this is only possible for certain types of actual behavior, such as optical signals with access to phase information. Other forms of actual behavior, such as intensity distributions, however do not allow this or only allow this incompletely. In these cases, it may even be necessary by way of assumption and incremental optimization of simulated refractive index profiles to determine the refractive index profile which approximately generates the actually observed actual behavior in the examination zone. Possibilities to this end are, for example, the application of Gerchberg-Saxton algorithms (R. W. Gerchberg and W. O. Saxton, "A Practical Algorithm for the Determination of Phase from Image and Diffraction Plane Pictures", Optik 35, 237 (1971)) or the application of trial-and-error processes such as simulated annealing, or else the application of genetic algorithms. In this case, it may become necessary to calculate the light propagation from the processing zone to the examination zone for a multiplicity of refractive index profiles during the incremental optimization, for example by use of ray tracing, and to compare the respective resultant behavior with the true actual behavior. If the deviations between the simulated and observed actual behavior are sufficiently small (for example deviations of the order of detection noise), it is possible to assume that the simulated refractive index profile sufficiently corresponds to the actual refractive index profile such that the difference thereof from the target refractive index profile then corresponds to the required change profile.

From this, a scanning pattern of focal spots of pulsed processing laser radiation of the laser processing apparatus is then determined for the purposes of processing at least one region of the transparent organic or inorganic material in the processing zone for implementing the change profile of the refractive index in the processing zone, with the goal of achieving the target distribution of the refractive index in the processing zone, and hence for establishing the target behavior of the indicator structure in the examination zone.

Finally, the control data for the control unit of the laser processing apparatus are determined therefrom for the purposes of implementing the scanning pattern.

According to example embodiments of the invention, the steps of the planning method are repeated at (temporally) predetermined intervals. In this case, the most recently implemented characterization of the actual behavior of the indicator structure in the examination zone is adopted as new actual behavior. Thus, if the steps of such a planning method are used again, for example after a partial implementation of the scanning pattern, this means monitoring the success of the previously rendered control data and providing an option for correcting the control data determined in the preceding iteration. As a result, a laser-induced change in the refractive index can be carried out in such a way that the desired target behavior in the examination zone can really be attained.

In an advantageous example variant, the change profile is adapted in such a way in the process that an under-correction is present (e.g., 75% to 90% of the required refractive index change). This prevents the occurrence of a partial over-correction caused by possibly unavoidable tolerances, such as laser fluctuations or patient-specific tissue reactions, which over-correction may not be able to be removed again or may only be removed again with much difficulty, for example by changing the refractive index of all non-over-corrected points in the processing zone. In this case, the magnitude of the under-correction can still be optimized by an analysis of the first processing steps, for example for minimizing the number of required processing steps and hence for minimizing the processing time.

In a generalization of the method according to the invention, the radiation or else waves of another processing energy source can be used instead of the pulsed laser radiation of the laser processing apparatus, provided energy influx into the processing zone is possible by application of said other processing energy source, and provided this can bring about a change in the refractive index. The planning method presented here can contribute to a substantially more accurate attainment of the target behavior in the examination zone, independently of the type of processing energy source, provided that there is "traversing" or scanning of the region to be processed in the processing zone in this case. In this case, processing radiation can be scanned in the processing zone or processing waves can be aligned in accordance with the control data, wherein the energy applied to this end in each case likewise is stored in the control data. Thus, the target can be achieved for example by low energy processing radiation in the processing zone and multiple scanning of the region to be processed or—if a very irregular change profile of the refractive index is implemented—partial multiple scanning of the region to be processed where the change in the refractive index to be achieved is greater than in regions where only a minor change of the refractive index is required. Or else the target is achieved by way of a single scan or only a few repeated scans of the region to be processed in the case of a comparatively higher energy—particularly in the case of very regular change profiles of the refractive index—, and hence a target distribution of the refractive index in the processing zone is obtained. Not least, the respective local dwell time of processing radiation or processing waves from a processing energy source can be part of the control data.

Examples of possible processing energy sources include UV radiation (in particular in conjunction with UV-light changeable polymers), (highly focused) ultrasound or microwaves, heat and optionally processing energy that arises from other physical or chemical effects and acts in tissue-altering fashion, provided said processing energy can be applied in spatially precise fashion.

However, the change in the refractive index is usually set in laser-induced fashion (LIRIC) by way of the number of applied laser pulses (by way of example, femtosecond laser oscillators are typically at 80 MHz) or by way of the treatment time. According to the invention, an (optionally only local) refractive index change in relation to the preceding actual measurement is recognized and processed during a repetition of the characterization of the actual behavior, and a new scanning pattern (a scanning pattern that has been altered in relation to the first scanning pattern) of focal spots of this pulsed processing laser radiation is determined therefrom.

The planning method according to the invention thus describes an intraoperative closed loop for measuring the effect of a laser-induced refractive index change. In an example embodiment of the planning method, the measurement of local changes of optical paths is used; in a further example embodiment, the imaging is evaluated through the treated regions.

The planning method according to the invention for example facilitates the planning of a highly precise refractive index change; even floaters can be treated accordingly. The planning method can be part of an LIRIC method with a closed-loop control circuit.

In principle, it is also conceivable that, for a patient's eye, the tissue is characterized in respect of all possible local refractive index variations in order to try to compensate for this one corresponding the treatment. However, structurally different and locally different tissue behavior (in respect of its processing) may occur in the process, and this can only be taken into account with difficulties.

An amplification of the effects of femtosecond laser radiation on the change of the refractive index in a processing zone—for example in the cornea of the patient's eye—can be achieved for example by the use of sodium fluorescein (see for example L. Nagy: Potentiation of Femtosecond Laser Intratissue Refractive Index Shaping (IRIS) in the Living Cornea with Sodium Fluorescein). In this case, the amplification effect can be taken into account in the planning method according to the invention.

Here, as already described above as a specific example embodiment variant, in a planning method according to the invention, a target distribution of the refractive index in a processing zone can be determined from the target behavior of the indicator structure in the examination zone, and an actual distribution of the refractive index in the processing zone can be determined from the actual behavior of the indicator structure in the examination zone.

In a specific example embodiment variant of the planning method according to the invention, indicator structures are used in a plurality of examination zones for the purposes of characterizing the actual behavior and defining the target behavior. These examination zones are arranged in the optical path upstream and downstream of the processing zone, and a behavior of an indicator structure in an examination zone upstream of the processing zone is compared to the behavior of the indicator structure in an examination zone downstream of the processing zone, and/or a behavior of an indicator structure in an examination zone arranged in the optical path downstream of the processing zone but not downstream of a region of the processing zone processed by use of the scanning pattern of focal spots is compared to the behavior of an indicator structure downstream of the region of the processing zone processed by use of the scanning pattern.

The comparison of the behavior of indicator structure in a plurality of examination zones in this case means relating the behavior of the indicator structures in the various examination zones to one another and in particular also recording a change in the behavior of the indicator structures in the various examination zones between a characterization at a first point in time and a characterization at a subsequent point in time.

The sought-after changes of the refractive index in the cornea can be 0.005, for example. In the case of a length or extent of the processing zone of significantly more than 10

µm (a mean extent can frequently be approximately 20 µm), the optical path between two indicator structures (which are also referred to as marker structures) would change by more than 50 nm, which would be a substantial, easily measurable effect in comparison with the known limits of phase-sensitive optical coherence tomography (OCT) with phase sensitivities down to values of less than 1 pm.

Suitable indicator structures can be tissue structures or tissue boundaries (such as layers of the cornea or the surface of the crystalline lenses). However, suitable indicator structures can also be provided by artificial structures such as refractive index change markers in an intraocular lens (IOL), which can be generated during the production or else intraoperatively by laser marking. Speckle patterns, for example in OCT scans, can also be suitable indicator structures, as long as they do not change or only change insubstantially by the processing such that the displacement thereof by the change in the optical path length change remains detectable.

It is also conceivable that only one indicator structure "downstream" (i.e., posterior) of the processing zone is sufficient if relative changes are easily identified.

In this case, in a planning method according to the invention, the influence of at least one zone which represents a distorting transmitting medium in the optical path of the examination radiation can be taken into account.

In an advantageous example embodiment of the planning method according to the invention, for characterizing the actual behavior use is made of the pulsed processing laser radiation of the laser processing apparatus, optionally with reduced energy, and/or at least one examination radiation from the range between x-ray radiation via the range of visible light and microwave radiation up to ultrasound. Here, at least one of the following processes is chosen for detection purposes: interferometric detection, optical coherence tomography (OCT), in particular using a phase-sensitive OCT system; confocal detection; fundus camera recordings, refractometric measurement, wavefront measurement, ultrasound imaging.

Accordingly, it is conceivable to use the treatment laser also for the characterization, for example as a femtosecond broadband light source for optical coherence tomography.

Instead of optical coherence tomography (OCT), other interferometric processes, which only detect relative optical path changes, are also conceivable with lasers, which only cover narrowband spectral ranges or which are virtually monochrome. However, this would require additional measures for selecting the recognition range, for example confocal filtering.

It is possible to use two-beam concepts like in the IOL master, that is to say mirror reflections of the patient's eye are used as a reference beam for optical coherence tomography, as a result of which independence of movement is ensured.

Confocal scanners can be used as an alternative to the optical coherence tomography: they are less sensitive but may be sufficient depending on the change to be detected.

When use is made of a circularly scanning femtosecond LIRIC system, a comparison of processed regions of the processing zone with regions outside of the processing zone or unprocessed regions of the processing zone by application of phase-sensitive optical coherence tomography (OCT) perpendicular to the scanning direction would be preferable, for example. Phase-sensitive OCT can be realized by parallel scanning beams or by subjecting the OCT beam to polarization splitting (Wollaston prism).

It may be useful to "convert" the change in the optical path of a characterization wavelength, for example 1060 nm, into a correction effect at a reference wavelength in the visible wavelength range of 400 . . . 700 nm, for example at 550 nm in the green, where there is a high sensitivity of the human eye. This is possible if knowledge about the dispersion behavior in the system is available or able to be determined.

In an advantageous example planning method according to the invention, the scanning pattern of focal spots for implementing the change profile of the refractive index is determined such that at least some of the processing zone is swept-over multiple times by the pulsed processing laser radiation, as already mentioned above.

As likewise already explained in the more general explanations above, the control data in an example planning method according to the invention comprise target coordinates of the focal spots, a pulse energy of the pulsed processing laser radiation and/or a processing time.

In a special planning method according to the invention, only a subset of the target coordinates of the focal spots in the processing zone are determined. Then, further target coordinates are interpolated between two target coordinates of this subset.

Thus, it is conceivable to carry out this "refractive index (change) analysis" for only a subset of treatment points in the processing zone, in this case of the focal spots of the pulsed laser radiation, and to interpolate the expected effect therebetween in order to save time. It is also conceivable to be flexible in relation to speed and precision depending on the requirement or specific refractive index profiles: thus, some portions may be less critical than others, it being possible to adapt the planning method thereto.

An example variant of the planning method according to the invention comprises a closed loop for tracking a change in the refractive index in the processing zone. This planning method is completed when a target behavior of the indicator structure and hence the desired change profile of the refractive index is implemented. Until this "success notification", the steps of the planning method are repeated again and again at predetermined time intervals.

The planning method according to the invention is furthermore advantageous for example if the transparent organic or inorganic material to be processed comprises a tissue of a patient's eye, in particular if the processing zone is arranged in at least one of the following regions of the patient's eye: cornea, natural lens or intraocular lens, and/or if the examination zone is arranged in the retina of the patient's eye.

A planning device for generating control data for a control unit of a laser processing apparatus for changing a refractive index in a processing zone of a transparent organic or inorganic material, the laser processing apparatus comprising a laser device with a laser source for generating pulsed processing laser radiation, a focusing apparatus for focusing the pulsed processing laser radiation on a focus in the processing zone and a scanning apparatus for scanning the focus of the pulsed processing laser radiation in the processing zone of the transparent organic or inorganic material and an examination apparatus which detects examination radiation for characterizing an actual behavior of an indicator structure in an examination zone using a detection apparatus, contains an interface for supplying data from the examination apparatus and an interface for transmitting control data to the control unit of the laser processing apparatus.

The control unit of the laser processing apparatus is configured to control the laser device, the focusing apparatus, the scanning apparatus and the examination apparatus. The control unit may comprise a plurality of partial units which are connected to one another, or else it may be configured as a central control unit which directly accesses the laser device, the focusing apparatus, the scanning apparatus and the examination apparatus.

The indicator structure whose actual behavior should be characterized can be arranged directly in the examination zone, or else represent an image representation of a structure in the processing zone in the examination zone.

Now, the planning device is configured to record the actual behavior of the indicator structure in the examination zone arranged in an optical path downstream of the processing zone of the transparent organic or inorganic material transilluminated by the examination radiation, to define a target behavior of the indicator structure in the examination zone, to determine a change profile of the refractive index in the processing zone from the difference between the actual behavior and the target behavior of the indicator structure in the examination zone, to determine a scanning pattern of focal spots of the pulsed processing laser radiation for processing the transparent organic or inorganic material in the processing zone for implementing the change profile of the refractive index in the processing zone—by modifying the organic or inorganic material along the scanning pattern-, and to establish the control data for the control unit of the laser processing apparatus for the scanning pattern of focal spots therefrom, it being possible to implement the change profile of the refractive index in the processing zone and obtain the target behavior of the indicator structure in the examination zone by use of said control data.

According to the invention, the planning device now is furthermore configured during a processing of the processing of the transparent organic or inorganic material in the processing zone, that is to say at predetermined intervals between two partial processing steps or directly during on-going processing of the transparent organic or inorganic material in the processing zone, to supply data from the examination apparatus, the data describing the actual behavior of the indicator structure, and transmit control data to the control unit of the laser processing apparatus, wherein—after a respective partial implementation of the scanning pattern—the most recently described behavior of the indicator structure in the examination zone is always adopted as new actual behavior of the indicator structure for the purposes of ascertaining the control data.

The predetermined intervals at which data from the examination apparatus are supplied to the planning device can be defined before or at the start of the method. However, a supply of data from the examination apparatus can also be implemented quasi-continuously.

As already described above for the planning method it is now also possible, in a generalization, for the planning device according to the invention to be used to generate control data for a control unit of a laser processing apparatus for changing a refractive index in a processing zone of a transparent organic or inorganic material to be used as a planning device for generating control data for a control unit of a processing apparatus for changing a refractive index in a processing zone of a transparent organic or inorganic material, in which radiation or else waves of another processing energy source are used to change a refractive index in a processing zone of a transparent organic or inorganic material, provided these facilitate an energy influx into the processing zone and the latter can bring about a change in the refractive index.

Thus, the planning device according to the invention can be used independently of the type of processing energy source—provided that there is "traversing" or scanning of the region to be processed in the processing zone in this case—, in order to contribute to a substantially more accurate attainment of the target behavior in the examination zone. In this case, processing radiation in the processing zone can be scanned or processing waves can be aligned in accordance with the control data.

For example, the energy to be applied to this end in each case is likewise stored in the control data: thus, the region of the processing zone to be processed, especially by way of comparatively low energy processing radiation in the processing zone which always only brings about a very small change in the refractive index at the currently processed position, can be described by the planning device using appropriate control data if a very irregular change profile of the refractive index is implemented with partial multiple scanning of the region to be processed where the change in the refractive index to be achieved is greater than in regions where only a minor change of the refractive index is required.

Not least, the respective local dwell time of processing radiation or processing waves from a processing energy source can be part of the control data to be generated by the planning device.

Examples of possible processing energy sources include UV radiation (in particular in conjunction with UV-light changeable polymers), (highly focused) ultrasound or microwaves, heat and optionally processing energy that arises from other physical or chemical effects and acts in tissue-altering fashion, provided said processing energy can be applied in spatially precise fashion.

The planning device according to the invention thus for example uses an intraoperative closed loop for measuring the effect of a laser-induced refractive index change. An example embodiment of the planning device according to the invention uses the measurement of local changes of optical paths; in a further example embodiment, the imaging is evaluated through the treated regions.

When using femtosecond laser radiation as pulsed processing laser radiation, it is possible to achieve an amplification of the effects on the change of the refractive index in a processing zone—for example in the cornea of the patient's eye—for example by the use of sodium fluorescein, and to take this amplification effect into account in the planning unit according to the invention.

An example embodiment of the planning device according to the invention is furthermore configured to determine a target distribution of the refractive index in a processing zone from the target behavior of the indicator structure in the examination zone and an actual distribution of the refractive index in the processing zone from the actual behavior of the indicator structure in the examination zone.

For example, the planning device according to the invention is furthermore configured to record the actual behavior of indicator structures in a plurality of examination zones and use these to define the target behavior, wherein these examination zones are arranged in the optical path upstream and downstream of the processing zone, and a behavior of an indicator structure in an examination zone upstream of the processing zone is compared to the behavior of the indicator structure in an examination zone downstream of the processing zone (that is to say, these are related to one another and/or the changes in the behavior thereof are also determined), and/or a behavior of an indicator structure in an examination zone arranged in the optical path downstream of the processing zone but not downstream of a region of the processing zone processed by use of the scanning pattern of focal spots is compared to the behavior of an indicator structure downstream of the region of the processing zone processed by use of the scanning pattern. It is advantageous here for the examination apparatus to use, for example, a phase-sensitive optical coherence tomography (OCT) device to this end.

As already mentioned above, tissue structures or tissue boundaries (such as layers of the cornea or the surface of the crystalline lenses) but also artificial structures such as refractive index change markers in an intraocular lens (IOL), which are generated during the production or else intraoperatively by laser marking, can be suitable indicator structures.

It is furthermore advantageous for example if the planning device according to the invention is configured to take account of the influence of at least one zone which represents a distorting transmitting medium in the optical path of the examination radiation.

In a particular configuration of the planning device according to the invention, for characterizing the actual behavior of the indicator structure use is made of the pulsed processing laser radiation of the laser processing apparatus, optionally with reduced energy, and/or at least one examination radiation from the range between x-ray radiation via the range of visible light and microwave radiation up to ultrasound, and one of the following apparatuses is chosen for detection purposes: interferometer, for example optical coherence tomography (OCT) device, in particular phase OCT system; confocal detector, fundus camera, refractometer, wavefront measuring device, ultrasound imaging system.

As already mentioned, other interferometric processes which only detect relative optical path changes using monochrome lasers are therefore also conceivable instead of optical coherence tomography (OCT). However, this requires additional measures for selecting the recognition range, for example confocal filtering. Further options and specific configurations were already mentioned above.

It is advantageous for example if the planning device according to the invention is configured to “convert” a change in the optical path of a characterization wavelength into a reference wavelength in the visible wavelength range. This is possible if knowledge about the dispersion behavior in the system is available.

A configuration of the planning device according to the invention is furthermore configured to determine the scanning pattern of focal spots for implementing the change profile of the refractive index such that at least some of the processing zone is swept-over multiple times by the pulsed processing laser radiation.

In a special example configuration of the planning device according to the invention, the control data comprise target coordinates of the focal spots, a pulse energy of the pulsed processing laser radiation and/or a processing time, and for example only a subset of the target coordinates of the focal spots in the processing zone are determined and further target coordinates are interpolated between two target coordinates of this subset.

Here, the planning device is for example configured to carry out this “refractive index (change) analysis” for only a subset of treatment points in the processing zone, in this case of the focal spots of the pulsed laser radiation, and to interpolate the expected effect therebetween in order to save time. It is also conceivable to be flexible in relation to speed and precision depending on the requirement or specific refractive index profiles: thus, some portions may be less critical than others, and an interpolation of target coordinates of the focal spots is only carried out in less critical regions while each individual focal spot is determined for the critical regions.

In a configuration of the planning device according to the invention, the transparent organic or inorganic material to be processed comprises a tissue of a patient’s eye, wherein in particular the processing zone is arranged here in at least one of the following regions of the patient’s eye: cornea, natural lens or intraocular lens, and/or wherein the examination zone is arranged in the retina of the patient’s eye.

A laser processing apparatus for processing a transparent organic or inorganic material comprises a laser device with a laser source for generating pulsed processing laser radiation, a focusing apparatus for focusing the pulsed processing laser radiation on a focus in the processing zone and a scanning apparatus for scanning the focus of the pulsed processing laser radiation in the processing zone of the transparent organic or inorganic material.

The laser processing apparatus furthermore comprises an examination apparatus which detects examination radiation for characterizing an actual behavior of an indicator structure in an examination zone using a detection apparatus, wherein the indicator structure in this case can be arranged directly in the examination zone or else can represent an image representation of a structure in the processing zone in the examination zone.

The laser processing apparatus according to the invention finally comprises a control unit for controlling the laser processing apparatus by use of control data, and a planning device, as described above, for generating control data for the control unit for the purposes of changing a refractive index in a processing zone of a transparent organic or inorganic material.

A computer program product according to the invention with program code is configured, when executed on a computer, to carry out the above-described planning method according to the invention for generating control data for a control unit of a laser processing apparatus for changing a refractive index in a processing zone of a transparent organic or inorganic material, and/or to be readable on an above-described planning device according to the invention for generating control data for a control unit of a laser processing apparatus for changing a refractive index in a processing zone of the transparent organic or inorganic material, in particular by a processor of such a planning device, and which, when executed by the planning device, generates control data in order to operate the laser processing apparatus according to the invention.

However, in a substantially more general example embodiment, a computer program product according to the invention can be configured to carry out the above-described planning method for generating control data for a control unit of a processing apparatus, which the radiation or else waves of another processing energy source for changing a refractive index in a processing zone of a transparent organic or inorganic material, and/or to be readable on an above-described planning device according to the invention for generating control data for a control unit of a processing apparatus, which uses the radiation or else waves of another processing energy source for changing a refractive index in a processing zone of a transparent organic or inorganic material, in particular by a processor of such a planning device, and which, when executed by the planning device, can generate control data in order to operate the laser processing apparatus according to the invention.

The above-described computer program product is stored on a computer-readable medium according to the invention.

In a method according to the invention for changing a refractive index in a transparent organic or inorganic material, control data for a laser processing apparatus for changing the refractive index using an above-described planning method are generated, and the transparent organic or inorganic material, in particular a tissue of a patient's eye, is processed by the laser processing apparatus with the aid of these control data.

BRIEF DESCRIPTION OF THE DRAWINGS

The present invention shall now be explained in more detail on the basis of example embodiments. In the figures.

DETAILED DESCRIPTION

Figure 1B:
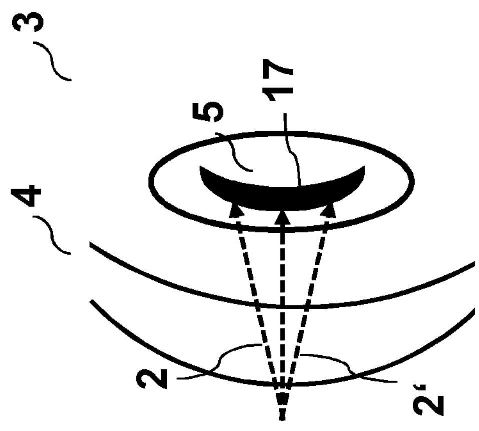
FIGS. 1*a* and 1*b* depict the principle of a laser-induced change in the refractive index (LIRIC) in a patient's eye according to the prior art, in a region of the cornea 4 or in an intraocular lens 5, as described above.
Figure 1A:
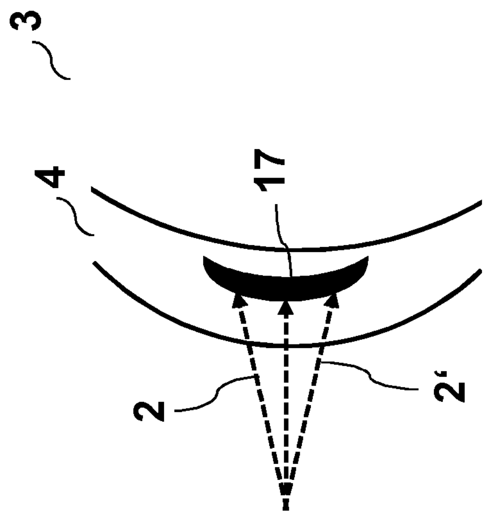
Figure 2:
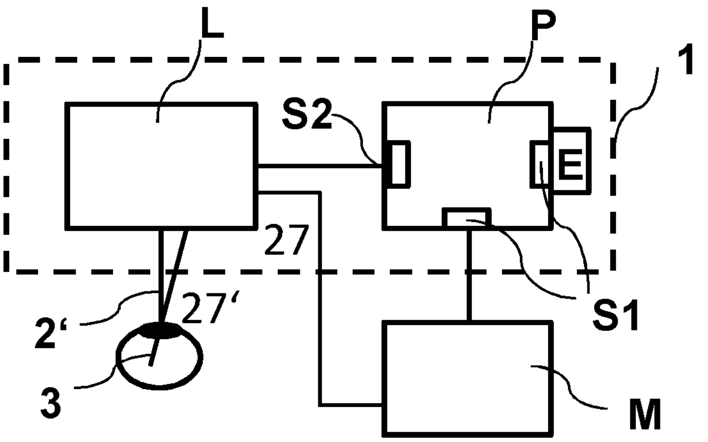
FIG. 2 depicts the diagram of a laser processing apparatus having a first planning device according to the invention.

FIG. 2 schematically depicts a laser processing apparatus 1 having a first planning device P according to the invention. In this variant, it has at least two devices or modules. A laser device L emits pulsed and focused processing laser radiation 2 toward the patient's eye 3. Here, the operation of the laser device L is implemented in fully automated fashion, that is to say the laser device L starts the deflection of the processing laser radiation 2 following an appropriate start signal and in the process generates modified regions in a processing zone 17 of a transparent organic or inorganic material. In its use as an ophthalmological laser processing apparatus 1, it generates modified regions in a processing zone 17 of a patient's eye, for example in the cornea 16, the natural lens or in the vitreous humor 6 of the patient's eye 3, but also in an artificial intraocular lens 5 in the patient's eye 3. The refractive index of the transparent organic or inorganic material is altered in these modified regions of the processing zone 17 as a result of the action of the processing laser radiation 2. The control data required for the operation are received by the laser device L in advance as a control data record from a planning device P via communication paths not denoted in any more detail, such as control lines, for example. Naturally, the communication can also be implemented in wireless fashion. As an alternative to direct communication, it is also possible to arrange the planning device P in spatially separated fashion from the laser unit L and to provide a corresponding data transmission channel. The transmission is for example implemented prior to the operation of the laser device L.

For example, the control data record is transmitted to the laser device L of the laser processing apparatus 1 via an interface S2 of the planning device P and, according to another example, an operation of the laser device L is blocked until a valid control data record is present at the laser device L. A valid control data record can be a control data record that, in principle, is suitable for use with the laser device L of the laser processing apparatus 1. However, additionally, the validity can also be linked to further tests being passed, for example whether specifications about the laser processing apparatus 1, e.g., an appliance serial number, or about the patient, e.g., a patient identification number, which are additionally stored in the control data record, correspond to other specifications that, for example, were read at the laser processing apparatus 1 or entered separately, as soon as the patient is in the correct position for the operation of the laser device L.

The planning device P produces the control data or the control data record, which is made available to the laser device L for implementing the operation, from the supplied data. Firstly, these are characterization data, which were ascertained by use of an examination apparatus M—using examination radiation 27—for the patient's eye 3 to be treated and which are supplied via an interface S1 for supplying characterization data from the planning device P. In particular, these are data from the characterization of an actual behavior of an indicator structure 18 in an examination zone 16 of the patient's eye 3, said data providing information about a processing zone 17 transilluminated in the process by the examination radiation 27, the pulsed and focused processing laser radiation 2 being intended to act, acting or having acted in said zone.

Further, target data are supplied via a further interface S1 and these contain a target behavior of the indicator structure 18 in the examination zone 17, with a (two- or three-dimensional) change profile of the refractive index in the processing zone 17 then being determined from the difference of the actual behavior and the target behavior of the indicator structure 18 in the examination zone 16. In this example embodiment, they are transmitted in automatic or manual fashion via an input device E to the planning device P by way of the interface S1.

In the present example embodiment, the characterization data originate from a separate examination apparatus M, which communicates with the planning device P of the laser processing apparatus 1. A direct radio or wired link of the examination apparatus M to the laser processing apparatus 1 in respect of the data transmission, which can be used in one variant for example, is advantageous in that the use of incorrect characterization data is excluded with the greatest possible reliability.

The control data generated by the planning device P determine the scanning pattern 15 of the focus 14 of the laser device L in a tissue or in a structure of the patient's eye 3, the control data rendering the laser processing apparatus 1 controllable in such a way that the change profile of the refractive index in the processing zone 17 is implementable as a result of processing the transparent organic or inorganic material, that is to say by processing the tissue or the structure, and—if the control data are used in the laser processing apparatus 1—is also implemented by an appropriate modification of the affected region in the processing zone 17 in accordance with the control data generated using the change profile of the refractive index.

Figure 3:
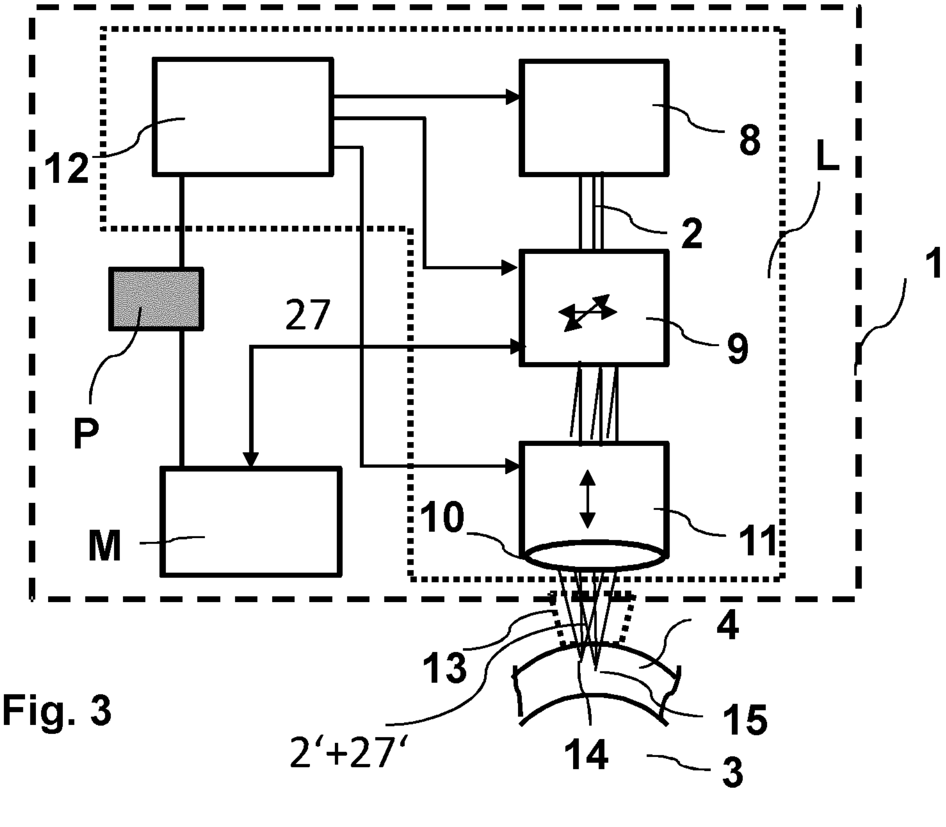
FIG. 3 depicts the diagram of a further laser processing apparatus according to the invention having a second planning device according to the invention, in which in particular the laser device is explained in more detail and the examination apparatus is also physically integrated.

FIG. 3 shows a second laser processing apparatus 1 according to the invention with a second planning device P according to the invention, again schematically, in which a laser device L and an examination apparatus M are fully integrated. This facilitates repeated, and in this case precisely repeatable, access to characterization data of the patient's eye 3. The planning device P, which satisfies the functions already described above, is integrated, at least temporarily, into the laser processing apparatus 1 and is in direct communication with the examination apparatus M and the control unit 12 of the laser device L.

In this example, the elements of the laser processing apparatus 1 and, in particular, of the laser device L comprised thereby are specified, but, in this case, too, only plotted to the extent that they are required for understanding the focal adjustment. The pulsed processing laser radiation 2, a femtosecond laser beam in this specific example, is focused on a focus 14 in a processing zone 17 of the patient's eye 3, for example in the cornea 4 thereof or in the vitreous humor 6 thereof, and the relative position of the focus 14 in the patient's eye 3 is adjusted along a scanning pattern 15 such that a modification of the affected region in the processing zone 17 is facilitated according to the control data in the control unit 12 (coordinates, pulse energies, processing time/number of scans in a region, etc., . . . ) which were generated using the change profile of the refractive index.

In this case, the patient's eye 3 is for example fixated by application of a patient interface 13 to the laser processing apparatus 1.

An xy-scanner 9, which is realized by two substantially orthogonally deflecting galvanometer mirrors in one variant, in this case deflects the pulsed processing laser radiation 2 emanating from the laser source 8 in two dimensions. Consequently, the xy-scanner 9 brings about an adjustment of the relative position of the focus 14 substantially perpendicular to the chief direction of incidence of the pulsed processing laser radiation 2 in the processing zone 17, that is to say in the cornea 4 or the vitreous humor 6 (in this example). In addition to the xy-scanner 9, a z-scanner 11 is provided for adjusting the depth position, said z-scanner being embodied as an adjustable telescope, for example. The z-scanner 11 ensures that the z-position of the relative position of the focus 14, i.e., the position thereof along the optical axis of incidence, is modified. The z-scanner 11 can be disposed upstream or downstream of the xy-scanner 9. The coordinates denoted below by x, y, z therefore relate to the deflection of the relative position of the focus 14.

Naturally, a person skilled in the art knows that the relative position of the focus 14 in a processing zone 17 can also be described in three dimensions by other coordinate systems; in particular, this need not necessarily be a rectangular coordinate system. Thus, it is not mandatory for the xy-scanner 9 to deflect about axes that are perpendicular to one another; rather, it is possible to use any scanner that is able to adjust the focus 14 in a plane not containing the axis of incidence of the processing laser radiation 2. Consequently, it is also possible to use oblique-angled coordinate systems, or else non-Cartesian coordinate systems.

For the purposes of controlling the relative position of the focus 14, the xy-scanner 9 and the z-scanner 11, which together realize a specific example of a three-dimensional scanning device 9, 11, are driven by a controller 12 via lines not denoted in any more detail. The same applies to the laser source 8 and the focusing apparatus 10. The same controller 12 (or a partial unit of the controller 12) controls the examination apparatus M. Thus, there is access to the different devices of the laser processing apparatus. The planning device P, which corresponds closely to the controller and can also physically be a part of the controller 12 in one variant, can therefore receive from the examination apparatus M the characterization data relating to the actual behavior of an indicator structure 18 in an examination zone 16, can compare these to a likewise supplied or defined target behavior of the indicator structure 18 in the examination zone 16 and can create a change profile of the refractive index in a processing zone 17 therefrom, and can ultimately ascertain from said change profile a scanning pattern 15 of focal points (focal spots) of pulsed processing laser radiation 2 of the laser processing apparatus 1 for the purposes of processing the material or the tissue and hence for the purposes of implementing the change profile of the refractive index in the processing zone 17, and can determine therefrom the control data for the control unit 12 of the laser processing apparatus 1 to carry out the scanning pattern 15, in principle at any time, and transfer said control data to the control unit 12.

This renders it possible to determine a change profile of the refractive index in the processing zone 17, to implement the change profile determined thus and to check and refine the implementation by repeating the planning method during the implementation in order to facilitate a precise correction of the refractive index. In particular, such a laser processing apparatus can be operated with a closed-loop method CL.

In this case, the examination radiation 27 from the examination apparatus M is supplied to the xy-scanner 9, for example in combination with the laser radiation 2 (for example via a beam splitter, a dichroic beam splitter, by application of polarization splitting or superposed at an angle) and is for example deflected together with the laser radiation 2 and focused together therewith by way of the focusing apparatus 10, wherein focused examination radiation 27' is generated, which may be superposed on the focused processing laser radiation 2'. However, in this case the focusing of the examination radiation 27' can slightly deviate from that of the laser radiation 2', for example in order to optimally measure indicator structures 18 in the examination zones 16-1 and 16-2 (see FIG. 4).

Figure 4:
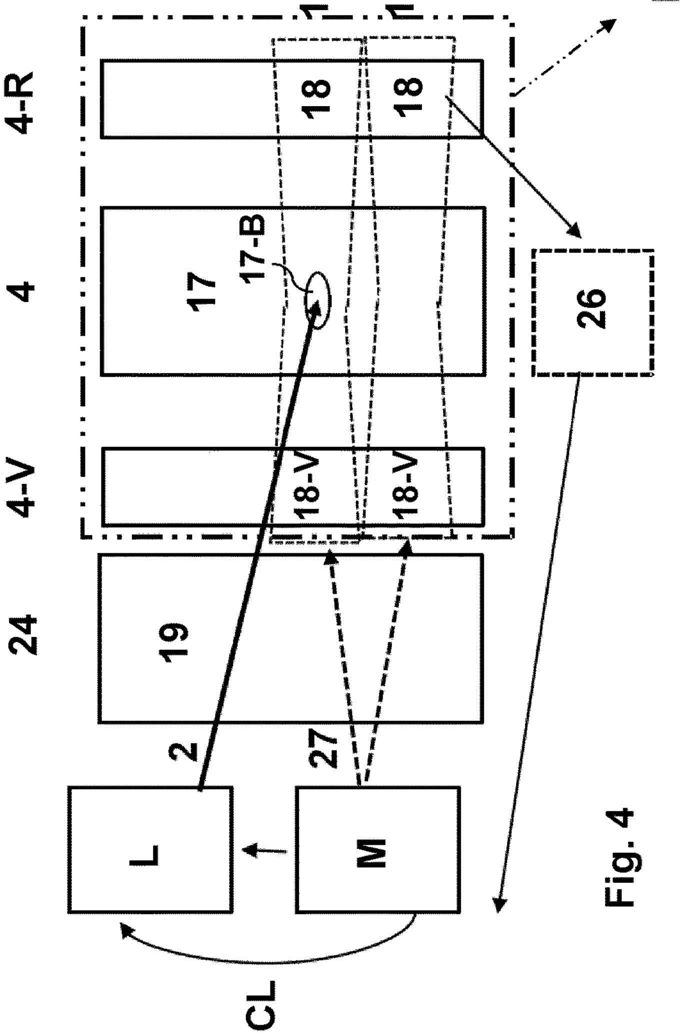
FIG. 4 depicts a schematic planning set up according to the invention for LIRIC processing of a region of the cornea for the purposes of obtaining a desired change in the optical path of a patient's eye, and FIG. 4*a* in turn shows an excerpt of FIG. 4 in the form of a real image representation of a very specific measurement set up.

FIG. 4 shows a schematic planning set up for LIRIC processing of a region of the cornea for the purposes of obtaining a desired change in the optical path of a patient's eye—for the purposes of setting the relative path length 26 by way of a change in the refractive index in the relevant region of the processing zone 17 of the cornea 4. The change in the refractive index in the processing zone 17 is caused by pulsed processing laser radiation 2 from a laser device L. By way of example, this can be implemented by heat-induced thermomechanical changes, in particular in collagen at different structure levels in natural eye tissue, by thermal expansion, stress generation and material contraction in the case of plastics such as PMMA or very generally by way of material changes by the use of fs lasers below the optical breakdown threshold (and hence without photodisruption) or above the optical breakdown threshold (i.e., with photodisruption). Examination radiation 27 is transmitted from a light source of an examination apparatus M to indicator structures 18, 18-V in various regions of one or more examination zones 16-1, 16-2 for the purposes of characterizing the actual behavior, wherein these examination zones 16-1, 16-2 are arranged along the optical path upstream and downstream of the processing zone 17, and a behavior of an indicator structure 18-V in an examination zone 16-1 upstream of the processed region 17-B of the processing zone 17 is compared to the behavior of the indicator structure 18 in an examination zone 16-1 downstream of the processed region 17-B of the processing zone 17, and/or a behavior of an indicator structure 18 in an examination zone 16-2, which is arranged in the optical path downstream of the processing zone 17 but not downstream of a region 17-B of the processing zone 17 processed by use of the scanning pattern 15 of focal spots, is compared to the behavior of an indicator structure 18 downstream of the region 17-B of the processing zone 17 processed by use of the scanning pattern 15. This actual behavior or the change in the actual behavior in the examination zone 16-1 of the cornea 4-V and 4-R upstream and downstream of the processed region 17-B of a processing zone 17 vis-à-vis the actual behavior in the examination zone 16-2 next to the processed region 17-B of the processing zone 17 is then compared to a defined target behavior.

In this case, the influence of a distorting transmitting medium 19, such as a tear film 24 in this case, is also taken into account.

The characterization data regarding the actual behavior, ascertained by operation of the examination apparatus M, are then used in the manner described above in order to generate in a planning device P the control data for a scanning pattern 15 of focal spots for the laser device L, the control data intending to implement the change profile of the refractive index for the purposes of adjusting the actual behavior to the target behavior. This can be repeated at any time, and so work can be carried out here in a closed loop CL method.

By way of example, if the required change of refractive index in the cornea is 0.005, the optical path between two indicator structures 18 will change by more than 50 nm in the case of a treatment zone length of at least 10 μm. Using an examination apparatus M which uses phase-sensitive optical coherence tomography (OCT), this effect is easily measurable in comparison with the known limits of phase-sensitive optical coherence tomography with phase sensitivities of down to less than 1 pm.

In this case, suitable indicator structures can be natural tissue structures or boundaries, but also artificially created structures.

Figure 4A:
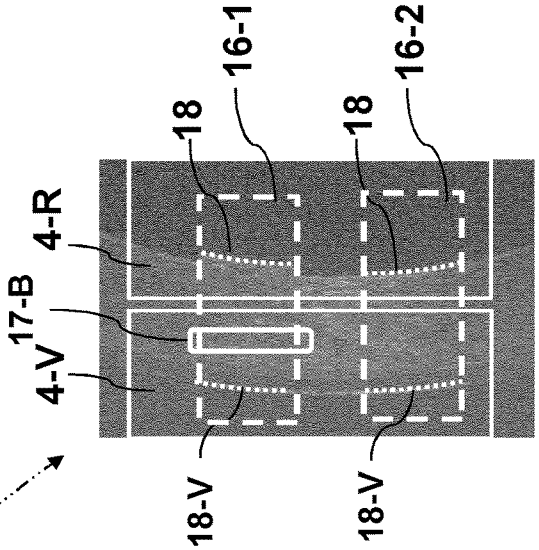

A very specific example embodiment of this planning set up of LIRIC processing of the cornea would lie in the use of a pulsed femtosecond laser L with an 80 MHz oscillator at a central wavelength of approximately 1064 nm, a phase-sensitive OCT at approximately 1060 nm as a measurement system M, by use of which it is possible to use an OCT measurement range 4-V with for example 5 . . . 500 μm scanning depth around the corneal front side and an OCT measurement range 4-R with for example likewise 5 . . . 500 μm around the corneal back side. The “corneal front side” indicator structure 18-V is compared to the “corneal back side” indicator structure 18 in the examination zone 16-1 (upstream and downstream of the processed region, that is to say the refractive index-modified zone) and additionally compared to the corneal front side 4-V indicator structure 18-V and the “corneal backside” 4-R indicator structure 18 in the examination zone 16-2 (next to the processed region)—using corneal pachymetry in the specific case. This is elucidated in FIG. 4*a*, which in turn shows an excerpt of FIG. 4 in the form of a real image representation with marking of corresponding structures in a very specific measurement set up, wherein the effect of the processing in the processed region 17-B on the relative position of the indicator structure 18 was represented here in exaggerated fashion for illustrative purposes: the OCT measurement regions extend over the respective corneal interfaces. However, the indicator structures 18, 18-V are the interfaces themselves, the signals of which are ascertained in the OCT measurement region.

Figure 5:
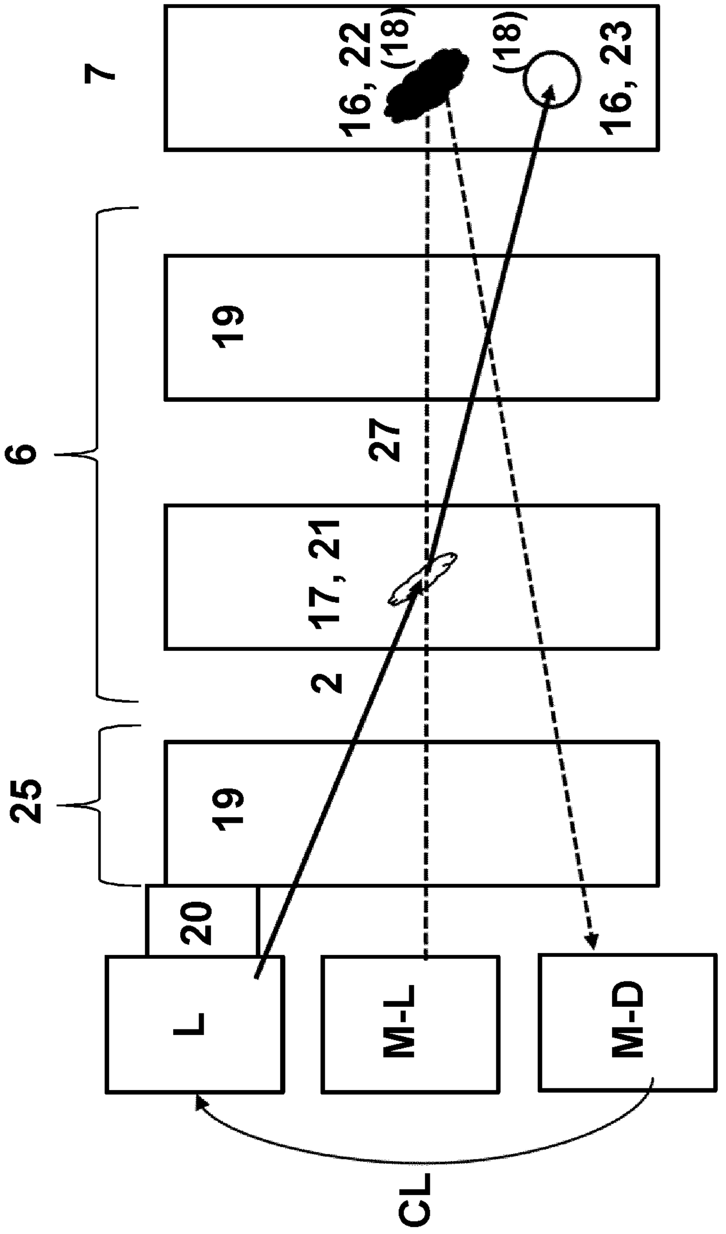
FIG. 5 depicts a schematic planning set up according to the invention for an LIRIC treatment of a transparent floater in the vitreous humor.

FIG. 5 illustrates a schematic planning set up for an LIRIC treatment of a transparent floater 21 in the vitreous humor 6: once again, the change in the refractive index in the processing zone 4 is caused by pulsed processing laser radiation 2 from a laser device L. Examination radiation 27 is projected from an observation light source M-L through the floater 21 in the processing zone 17 into an examination zone 16 on the retina 22 (and forms a virtual indicator structure (18) there) and the returning examination radiation 27 is detected by the detector of the examination apparatus M-D. Optionally, it is also possible to use the image representation 23 of the floater 21 by the processing laser radiation 2 as a virtual indicator structure (18) on the retina. In this case, too, the influence of distorting transmitting media in the light path 25 in the patient’s eye, including the lens and the vitreous humor 6 itself, is taken into account. An adaptive optical unit 20 can likewise be part of the optical path in this case and can be taken into account.

In this case, the transparent floater 21 is processed until its effect on the retina 22 as examination zone 16 is minimized. This also includes adjusting the refractive index around the floater 21.

The aforementioned features of the invention, which are explained in various example embodiments, can be used not only in the combinations specified in an exemplary manner but also in other combinations or on their own, without departing from the scope of the present invention.

A description of an apparatus relating to method features is analogously applicable to the corresponding method with respect to these features, while method features correspondingly represent functional features of the apparatus described.

The invention claimed is:

1. A planning method to generate control data for a control unit of a laser processing apparatus utilized in a surgical procedure to change a refractive index in a processing zone of a transparent organic or inorganic material, the method comprising:

characterizing an actual behavior of an indicator structure in an examination zone arranged in an optical path downstream of the processing zone of the transparent organic or inorganic material transilluminated by examination radiation;

defining a target behavior of the indicator structure in the examination zone;

determining a change profile of the refractive index in the processing zone from a difference between actual behavior of the indicator structure in the examination zone and the target behavior of the indicator structure in the examination zone;

determining a scanning pattern of focal spots of pulsed processing laser radiation of the laser processing apparatus for processing the transparent organic or inorganic material in the processing zone to implement the change profile of the refractive index in the processing zone;

determining control data for the control unit of the laser processing apparatus for implementing the scanning pattern; and repeating aforementioned steps iteratively at predetermined intervals, wherein the characterization of the actual behavior of the indicator structure in the examination zone implemented most recently is always adopted as a new actual behavior.

2. The planning method as claimed in claim 1, further comprising determining a target distribution of the refractive index in a processing zone from the target behavior of the indicator structure in the examination zone and determining an actual distribution of the refractive index in the processing zone from the actual behavior of the indicator structure in the examination zone.

3. The planning method as claimed in claim 1, further comprising using indicator structures in a plurality of examination zones for characterizing the actual behavior and for defining the target behavior, wherein:

the examination zones are arranged in the optical path upstream and downstream of the processing zone, and further comprising comparing a behavior of an upstream indicator structure in an examination zone upstream of the processing zone to behavior of a downstream indicator structure in an examination zone downstream of the processing zone, and/or comparing a behavior of an indicator structure in an examination zone arranged in the optical path downstream of the processing zone but not downstream of a region of the processing zone processed by application of the scanning pattern of focal spots to the behavior of an indicator structure downstream of the region of the processing zone processed by use of the scanning pattern.

4. The planning method as claimed in claim 1, further comprising taking into account an influence of at least one zone which represents a distorting transmitting medium in the optical path of the examination radiation.

5. The planning method as claimed in claim 1, further comprising making use of the pulsed processing laser radiation of the laser processing apparatus, at least one examination radiation from a range between x-ray radiation via the range of visible light and microwave radiation up to ultrasound for characterizing the actual behavior or both, and choosing at least one of the following processes for detection purposes: interferometric detection including optical coherence tomography (OCT) and a phase-sensitive OCT, confocal detection; fundus camera recordings, refractometric measurement, wavefront measurement and ultrasound imaging.

6. The planning method as claimed in claim 1, further comprising determining the scanning pattern of focal spots for implementing the change profile of the refractive index such that at least some of the processing zone is swept-over multiple times by the pulsed processing laser radiation.

7. The planning method as claimed in claim 1, wherein the control data comprise at least one of target coordinates of the focal spots, a pulse energy of the pulsed processing laser radiation and a processing time.

8. The planning method as claimed in claim 7, further comprising determining only a subset of the target coordinates of the focal spots in the processing zone and interpolating further target coordinates between two target coordinates of this subset.

9. The planning method as claimed in claim 1, further comprising using a closed loop for tracking a change in the refractive index in the processing zone and completing the closed loop when the target behavior of the indicator structure and hence the desired change profile of the refractive index is implemented.

10. The planning method as claimed in claim 1, wherein the transparent organic or inorganic material to be processed comprises a tissue of a patient's eye; and wherein the processing zone is arranged in at least one of the following regions of the patient's eye: a cornea, a natural lens or an intraocular lens, and/or wherein the examination zone is arranged in the retina of the patient's eye.

11. The planning method as claimed in claim 1, wherein the processing zone is arranged in at least one of the following regions of the patient's eye: a cornea, a natural lens or an intraocular lens, and/or wherein the examination zone is arranged in the retina of the patient's eye.

12. A computer program product with program code which, when executed on a computer, carries out the planning method for generating control data for a control unit of a laser processing apparatus for changing a refractive index in a processing zone of a transparent organic or inorganic material as claimed in claim 1.

13. A method for changing a refractive index in a transparent organic or inorganic material, comprising:

generating control data for a laser processing apparatus for changing the refractive index using a planning method as claimed in claim 1, and processing the transparent organic or inorganic material, including a tissue of a patient's eye, by the laser processing apparatus with aid of the control data.

14. A planning device to generate control data for a control unit of a laser processing apparatus to change a refractive index in a processing zone of a transparent organic or inorganic material, the laser processing apparatus comprising:

a laser device with a laser source that generates pulsed processing laser radiation;

a focusing apparatus that focuses the pulsed processing laser radiation at a focus in the processing zone;

a scanning apparatus that scans the focus of the pulsed processing laser radiation in the processing zone of the transparent organic or inorganic material; and an examination apparatus that detects examination radiation to characterize an actual behavior of an indicator structure in an examination zone using a detection apparatus, wherein the planning device comprises an interface that supplies data from the examination apparatus and an interface that transmits control data to the control unit of the laser processing apparatus, and wherein the planning device is configured:

to record the actual behavior of the indicator structure in the examination zone arranged in an optical path downstream of the processing zone of the transparent organic or inorganic material transilluminated by the examination radiation, to define a target behavior of the indicator structure in the examination zone, to determine a change profile of the refractive index in the processing zone from a difference between the actual behavior and the target behavior of the indicator structure in the examination zone, to determine a scanning pattern of focal spots of the pulsed processing laser radiation for processing the transparent organic or inorganic material in the processing zone for implementing the change profile of the refractive index in the processing zone, and to establish the control data for the control unit of the laser processing apparatus therefrom, wherein the planning device is furthermore configured to, repeat iteratively at predetermined intervals during the processing of the transparent organic or inorganic material in the processing zone, supply data from the examination apparatus, the data describing the actual behavior of the indicator structure, and configured to transmit control data to the control unit of the laser processing apparatus, wherein most recently described behavior of the indicator structure in the examination zone is always adopted as new actual behavior of the indicator structure for the purposes of ascertaining the control data.

15. The planning device as claimed in claim 14, furthermore configured to determine a target distribution of the refractive index in a processing zone from the target behavior of the indicator structure in the examination zone and an actual distribution of the refractive index in the processing zone from the actual behavior of the indicator structure in the examination zone.

16. The planning device as claimed in claim 14, furthermore configured to record the actual behavior of indicator structures in a plurality of examination zones and use these to define the target behavior, wherein at least one of the plurality of examination zones is arranged in the optical path upstream and downstream of the processing zone, and a behavior of an indicator structure in an examination zone upstream of the processing zone is compared to the behavior of the indicator structure in an examination zone downstream of the processing zone, and a behavior of an indicator structure in an examination zone arranged in the optical path downstream of the processing zone but not downstream of a region of the processing zone processed by use of the scanning pattern of focal spots is compared to the behavior of an indicator structure downstream of the region of the processing zone processed by the use of the scanning pattern.

17. The planning device as claimed in claim 14, furthermore configured to take account of influence of at least one zone which represents a distorting transmitting medium in the optical path of the examination radiation.

18. The planning device as claimed in claim 14, wherein, for characterizing the actual behavior of the indicator structure, use is made of at least one of the pulsed processing laser radiation of the laser processing apparatus and at least one examination radiation from a range between x-ray radiation via the range of visible light and microwave radiation up to ultrasound, and wherein one of the following apparatuses is chosen for detection purposes: an interferometer including optical coherence tomography (OCT) and a phase-sensitive OCT, a confocal detector, a fundus camera, a refractometer, a wavefront measuring device and an ultrasound imaging system.

19. The planning device as claimed in claim 14, furthermore configured to determine the scanning pattern of focal spots to implement the change profile of the refractive index such that at least some of the processing zone is swept-over multiple times by the pulsed processing laser radiation.

20. The planning device as claimed in claim 14, wherein the control data comprise at least one of target coordinates of the focal spots, a pulse energy of the pulsed processing laser radiation and a processing time.

21. The planning device as claimed in claim 14, wherein the transparent organic or inorganic material to be processed comprises a tissue of a patient's eye; and wherein the processing zone is arranged in at least one of the following regions of the patient's eye: a cornea, a natural lens or an intraocular lens, and/or wherein the examination zone is arranged in the retina of the patient's eye.

22. A laser processing apparatus for processing a transparent organic or inorganic material, comprising a laser device with a laser source for generating pulsed processing laser radiation;

a focusing apparatus for focusing the pulsed processing laser radiation on a focus in the processing zone;

a scanning apparatus for scanning the focus of the pulsed processing laser radiation in the processing zone of the transparent organic or inorganic material;

an examination apparatus which detects examination radiation for characterizing an actual behavior of an indicator structure in an examination zone using a detection apparatus, a control unit for controlling the laser processing apparatus by means of control data, and a planning device for generating control data for the control unit, as claimed in claim 14.

23. A computer program product with program code which is readable on a planning device for generating control data for a control unit of a laser processing apparatus for changing a refractive index in a processing zone of the transparent organic or inorganic material as claimed in claim 14, including by a processor of such a planning device, and which, when executed by the planning device, generates control data in order to operate the laser processing apparatus.

* * * * *